(12) United States Patent
Maisnik

(10) Patent No.: US 6,230,711 B1
(45) Date of Patent: May 15, 2001

(54) MULTIPURPOSE SECUREMENT STRIP

(76) Inventor: Hugo Josiah Maisnik, 1986 Verde Vista Dr., Monterey Park, CA (US) 91754

(*) Notice: Subject to any disclaimer, the term of this patent is extended or adjusted under 35 U.S.C. 154(b) by 0 days.

(21) Appl. No.: 08/775,874

(22) Filed: Jan. 2, 1997

(51) Int. Cl.$^7$ .................................................. A61B 19/00
(52) U.S. Cl. .......................................... 128/869; 128/876
(58) Field of Search ................................... 128/845, 846, 128/869, 875, 876; 602/19; 2/311, 312, 318, 402, 403

(56) References Cited

U.S. PATENT DOCUMENTS

| | | | |
|---|---|---|---|
| 4,292,963 | * 10/1981 | Ford | 602/21 |
| 4,319,571 | * 3/1982 | Winchell | 128/DIG. 24 |
| 4,695,679 | * 9/1987 | Strauss | 174/117 FF |
| 5,386,595 | * 2/1995 | Kuen | 2/402 |

* cited by examiner

*Primary Examiner*—Michael A. Brown
(74) *Attorney, Agent, or Firm*—Terrell P. Lewis

(57) ABSTRACT

The instant invention relates to a multipurpose glueless securement means for fastening/sealing applications which traditionally are accomplished by the use of a disposable adhesive bearing tape/or a disposable tape utilizing mechanical fastening devices. More particularly, the invention relates to the use of a high tensile strength polyvinyl chloride (PVC) strip which possesses self-adhesive properties and can be reused virtually indefinitely. Due to the unique chemical properties of the invention it has a wide range of useful applications from traditional sealing or binding applications to applications involving contact or application with external skin surfaces.

14 Claims, 1 Drawing Sheet

MULTIPURPOSE SECUREMENT STRIP

FIELD OF THE INVENTION

The invention relates to a reusable multipurpose securement means for fastening sealing applications which traditionally are accomplished by the use of a disposable adhesive bearing tape and/or a disposable tape utilizing mechanical fastening means. More particularly, the invention relates to the use of a high tensile strength polyvinyl chloride (PVC) strip which possesses self-adhesive properties and can be reused virtually indefinitely. Additionally, the invention finds use in a wide range of diverse applications such as binding articles or sealing packages to applications wherein the invention is utilized in association with external skin surfaces.

BACKGROUND OF THE INVENTION

It is well known to employ a multitude of transparent flexible film wrapping material, including thermoplastic polymeric films, for wrapping articles such as foodstuffs, as disclosed in U.S. Pat. Nos. 3,429,717; 5,422,151; and 5,387,470. Additionally, U.S. Pat. No. 4,367,256 discloses a polyethylene film wrapping material. U.S. Pat. No. 5,240,535 discloses the use of a vinyl strap for the limited purpose of securing safety equipment to the external clothing of a hockey player. However, these types of thin flexible polymeric films do not possess the required levels of tensile strength that would allow for sealing and/or binding applications where great strength is required but where also significant flexibility is required. More particularly, there are a multitude of available traditional and specialty oriented tapes or securement products such as disposable adhesive-bearing tapes, usually of paper or elastic composition, such as Scotch Brand Masking Tape and Scotch Brand disposable clear adhesive tape made by the 3M corporation. Additionally, there are a large number of cloth, filament or fiber-based tape products available that utilize either adhesive fastening means and/or some form of mechanical fastening means.

The problems associated with the use of traditional adhesive-bearing paper tapes (cohesively acting fastening means) or tapes utilizing mechanical fastening or locking means are two fold: (1) economic considerations based upon the non-reusable nature of these products; and (2) adhesive-bearing tapes or tapes utilizing mechanical fastening or locking means are often manufactured from various types of paper, elasticized-paper or elasticized-cloth material, and as such these materials possess different inherent characteristics (tensile strengths) that directly affect their ability to withstand externally applied forces such as object weight, direct pressure or trauma caused by rough handling, moisture, heat, etc. Other products intended for use as sealing or securement means such as straps bearing VELCRO or straps bearing buckles or buttons all have very severe limitations such as difficulty in application and removal because of the great amount of physical effort that is required and the great tendency of VELCRO and tapes to become entangled with other objects that they come into contact with as well as entangled with themselves. Additionally, a tape may possess all the necessary properties for a particular application, but be deficient in that it does not possess the necessary tensile strength or is not capable of reuse or adjustment once it has been initially applied.

The instant invention simulates all essential properties of disposable adhesive-bearing tapes and/or tapes utilizing mechanical binding means in that it can be applied in a manner identical to that with which disposable tape is applied. Specifically, polyvinyl chloride is virtually inelastic. This property facilitates its mechanical functioning, and accounts for its similarity in "feel" to disposable adhesive-bearing tape. Furthermore, the electrostatic, intramolecular, self-adhesive property of polyvinyl chloride renders unnecessary the use of any adhesive or mechanical fastening device to achieve a strong, yet readily reversible, fastening or binding, which is achieved by merely overlapping portions (ends) of the invention. In addition, the self-clinging properties of the invention allow the invention to overcome the inherent problems associated with the use of adhesive-bearing tapes, cloth-type bandages and/or wrappings in many applications, including medical applications and procedures, by providing for quick application, removal and/or subsequent adjustment of the invention once it has been applied to the patient. The inability of traditional adjesive-bearing tapes, bandages, straps, belts etc. to be removed and/or adjusted without the need for a significant expenditure of effort with a corresponding level of trauma caused by adhesion of such products to the skin surface combined with the lack of reuse capability have represented long felt needs by endusers.

It is therefore an object of the invention to provide a multi-purpose tape structure that possesses strong self-adhesive/self-clinging properties without the need for any externally applied adhesives or mechanical fastening means.

It is another objective of the invention to provide a multipurpose tape structure that possesses sufficient inherent tensile strength to allow for the application of the invention under extreme advers conditions of weight, pressure, heat, moisture, etc. while being capable of quick removal and reapplication virtually an unlimited number of times.

It is yet another object of the invention to provide for a multipurpose tape structure that when utilized in association with the skin of a patient provides a securement means that has the ability to be quickly and easily applied, removed and reapplied an infinite number of times without the trauma and irritation associated with the use and removal of conventional tapes and bandages. These and other objects of the invention will be readily apparent to those skilled in the art from the following disclosure and appended claims.

SUMMARY OF THE INVENTION

The instant invention involves the use of double pressed polished PVC strips that provide a securement or sealing means for applications where a strong binding or sealing capability is required, such as use with packages and books or where a quick and easily applied binding or sealing means is required. Additionally, the instant invention involves securement means that are readily and easily removed allowing for adjustment and/or complete reapplication, such as with papers, letters or similarly situated items. Further, due to the chemical electrostatic molecular "binding or bonding" properties of the tape the invention may be utilized in widely varying and diverse applications such as the binding or sealing of articles such as boxes, books, documents and related articles to uses in association with skin surfaces wherein the trauma associated with the application and removal of traditional adhesive-bearing tapes or bandages can be avoided.

PVC possesses sufficient tensile strength to be utilized in sealing or binding applications where the weight of the object to be secured or bound is significant and where there may be significant external pressures at play as well. In this regard the instant invention discloses a double pressed polished PVC securement strip or "tape" that possesses increased self-clinging or binding properties that are not present in other polymeric films or in other vinyl formulations. While many polymeric films and related materials undergo a finishing process that involves polishing and related procedures they do not incorporate a double pressed polished procedure that involves the double pressing and polishing of both surfaces of the PVC as a final processing step in the manufacturing procedure of the product. This double pressed polished procedure results in a greater level of electrostatic, intra-molecular surface phenomena that in turn results in significantly increased self-clinging or binding properties. It is this increased self-clinging or binding capability that follows for the use of the invention in a multitude of applications where a strong sturdy seal is required, such as during the sealing of packages or other related uses, but at the same time provides for easy removal and reapplication, i.e., reuse of the invention. Unlike the present invention other polymeric films and/or vinyl tapes do not possess this enhanced self-clinging capability, high tensile strength and reusable capability inherent in the present invention.

DETAILED DESCRIPTION OF THE PREFERRED EMBODIMENT

Figure 1:
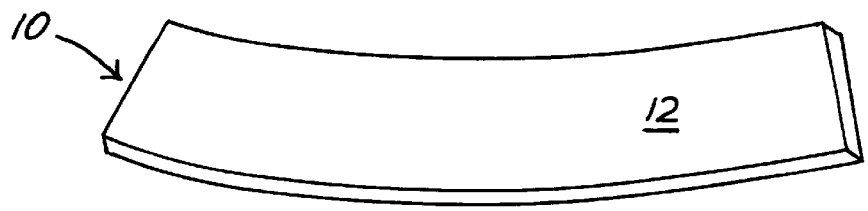
FIG. 1 is a perspective view of a preferred embodiment of the strip of the present invention.
Figure 2:
FIG. 2 is a side view of the strip shown in FIG. 1.

As seen in FIGS. 1 and 2, the tape 10 of the present invention comprises an elongated rectangular inelastic strip 12 of double pressed polished PVC. The double pressed polished finishing procedure utilized in the manufacture of the instant invention, as described herein, results in a vinyl strip that is capable of performing a multitude of fastening, sealing and/or securement applications such as sealing packages, boxes, binding books and papers and other articles. Additionally, the tape 10 (as shown in FIG. 3b where the tape is used to secure a person's leg to a support S) of the instant invention is capable of skin contact as it does not produce the trauma to the skin surface that adhesive bearing tapes, strips or bandages cause, especially upon removal and attempted reuse.

Figure 3A:
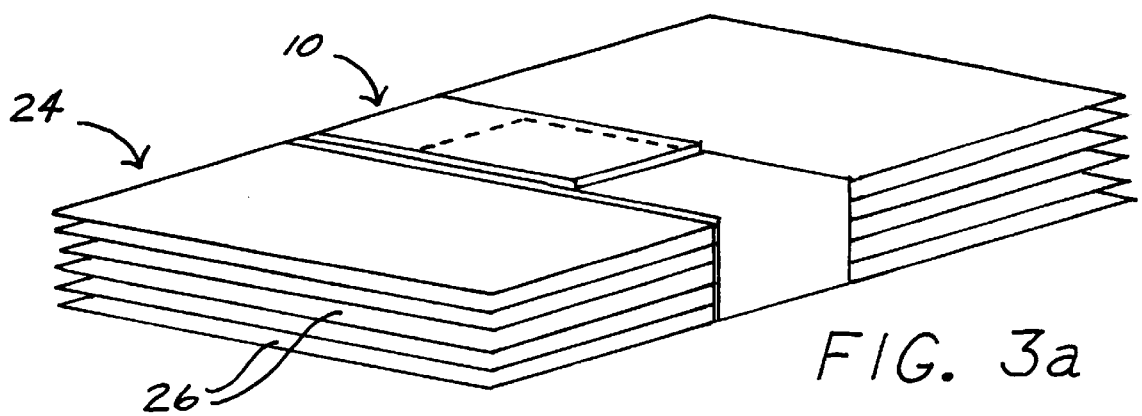
FIGS. 3a and 3b show the strip of the invention used to secure stack of sheets and to secure a person's limb to a support, respectively.
Figure 3B:
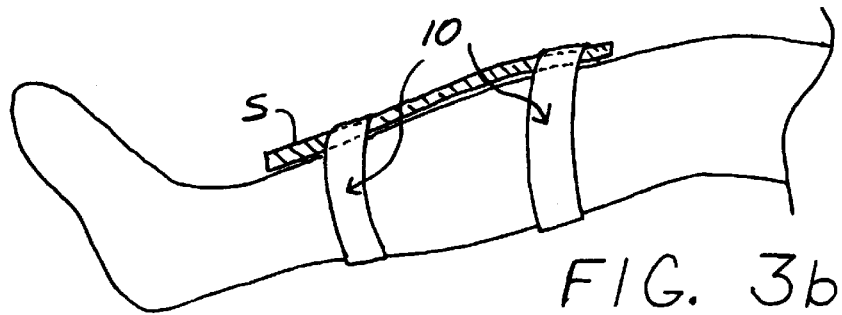

FIG. 3a shows the tape of the instant invention applied about the exterior surface of the package or article 24 (shown in FIG. 3a to comprise plural layers of material) that is to be sealed or secured in such a manner that the ends of the strip overlap one another resulting in a stron self-seal or securement. The strips of PVC may be in any desired width and length but in a preferred embodiment the strips are from ½ inch to 2½ inches in width and between 50 inches and 500 inches in length. Additionally, due to the inherent tensile strength of the double pressed polished PVC and because of the enhanced intra-molecular electrostatic self-clinging properties of the invention only one layer of the instant invention is required for most sealing and/or securement applications.

In a preferred embodiment the elongated rectangular strips of tape are comprised of 8 to 14-gauge double pressed polished PVC in thicknesses of from three (3) one-thousandths of an inch to ten (10) one-thousandths of an inch.

In another embodiment, the tape of the instant invention is transparent but can also be in any solid color. Additionally, the tape can be sterilized by traditional non-heat-based methodologies.

The tape, when used in medical applications, such as for securing a person's limb to a support (FIG. 3b), can possess antifungal and antimicrobial properties due to the invention's ability to be treated with traditional antifungal and anti-microbial agents without the loss of any structural or functional properties or capabilities.

The use of double pressed polished PVC for this invention, with its enhanced electrostatic self-clinging/ binding properties, results in the ability of the user to apply the invention with the peace of mind that he will not have to utilize excessive amounts of it and that he will be able to quickly and easily remove and reuse it. The economic and related environmental advantages of the instant invention are thus self evident.

It will be apparent that the invention is not limited to the embodiments described above and that variations and modifications may be made thereto within the scope of the invention.

What is claimed:

1. An all purpose securement strip, comprising: an elongated rectangular strip of 8 to 14-gauge double pressed polished polyvinyl chloride, said strip being between three (3) one-thousandths of and inch and ten (10) one-thousandths of an inch in thickness, said strip further characterized as possessing physical and chemical properties that instill into said strip self-binding properties and allow for said strip to be applied and removed rapidly for an infinite number of reuses.

2. The strip of claim 1 wherein said double pressed polished polyvinyl chloride is transparent.

3. The strip of claim 1 wherein said strip is between five (5) one-thousandths of an inch and (10) one-thousandths of an inch in thickness.

4. The strip of claim 1 wherein said strip is between ½ inch and 2½ inches in width.

5. The strip of claim 1 wherein said strip is reusable.

6. The strip of claim 1 wherein said strip possesses antifungal and anti-microbial properties.

7. A method of securing an article, comprising: application of a strip of double pressed polished polyvinyl chloride to an article and overlapping the ends of said strip to form a self-binding seal, said strip further comprising a rectangular elongated strip of 8 to 14-gauge double pressed polished polyvinyl chloride being between three (3) one-thousandths of an inch and ten (10) one-thousandths of an inch in thickness and between ½ inch and 2½ inches in width, said strip further characterized as possessing physical and chemical properties that instill into said strip self-binding properties that allow for said strip to be applied and removed rapidly for infinite reuse.

8. The method of claim 7 wherein said strip is transparent.

9. The method of claim 7 wherein said strip is in a thickness of between five (5) one-thousandths of an inch and ten (10) one-thousandths of an inch.

10. A method of securing a limb of a patient to a support surface to immobilize said limb during medical procedures by securing said limb to said support surface by wrapping a strip of double pressed polished polyvinyl chloride around said limb and said support surface and overlapping the ends of said strip to form a self-binding seal, said strip comprising: a rectangular elongated strip of 8 to 14-gauge perforated double pressed polished polyvinyl chloride, said strip being between three (3) one-thousandths of an inch and ten (10)

one-thousandths of an inch in thickness, said strip being between ½ and 2½ inches in width and in customizable lengths, said strip being transparent.

11. The method of claim 10 wherein said strip is between five (5) one-thousandths of an inch and ten (10) one-thousandths of and inch in thickness.

12. The method of claim 10 wherein said strip is reusable.

13. The method of claim 10 wherein said strip is sterilizable by traditional non-heat-based methodologies.

14. The method of claim 10 wherein said strip possesses antifungal and anti-microbial properties.

* * * * *